United States Patent [19]

Sarantakis et al.

[11] 4,097,471
[45] Jun. 27, 1978

[54] POLYPEPTIDES WITH MORPHINE-LIKE ACTIVITY

[75] Inventors: Dimitrios Sarantakis, West Chester; Larry Stein, Haverford, both of Pa.

[73] Assignee: American Home Products Corporation, New York, N.Y.

[21] Appl. No.: 800,678

[22] Filed: May 26, 1977

[51] Int. Cl.$^2$ .................... C07C 103/52; A61K 37/00
[52] U.S. Cl. ............................. 260/112.5 R; 424/177
[58] Field of Search ................. 260/112.5 R; 424/177

[56] References Cited

PUBLICATIONS

J. D. Belluzzi, Proc. Natl. Acad. Sci. USA 73, 1976, pp. 3308–3310.

L. Graf, et al., Febs. Letter 64, 1976, pp. 181–184.

Primary Examiner—Delbert R. Phillips
Attorney, Agent, or Firm—Richard K. Jackson

[57] ABSTRACT

The polypeptide H-Tyr-Gly-Gly-Phe-Leu-Thr-Ser-Glu-Lys-Ser-Gln-Thr-Pro-Leu-Val-Thr-OH, or a nontoxic salt thereof, exerts an analgesic effect in rats when injected into the lateral brain ventricle.

2 Claims, No Drawings

POLYPEPTIDES WITH MORPHINE-LIKE ACTIVITY

BACKGROUND OF THE INVENTION

Enkephalin, a natural opiate receptor agonist in the brain, has been indentified [see Hughes et al., Nature, 256, 577 (1975)] as a mixture of two pentapeptides: H-Tyr-Gly-Gly-Phe-Met-OH (methionine-enkephalin) and H-Tyr-Gly-Gly-Phe-Leu-OH (leucine-enkephalin). Both peptides mimic the ability of morphine to block electrically evoked contractions of mouse vas deferens and guinea pig ileum, and both inhibit the stereospecific receptor binding of the opiate antagonist 3H-naloxone in brain homogenates.

It has been proposed that enkephalin receptors may be sites at which morphine-like drugs exert their analgesic activities, and that enkephalin may be the modulator or transmittor in brain systems for pain suppression or analgesia. It has been reported that methionine-enkephalin and leucine-enkephalin, when administered by injection in the brain ventricle in rats, induce a profound analgesia that is fully reversible by naloxone. [See Beluzzi et al., Nature, 260, 625 (1976)]. The enkephalins are inactive when administered peripherally, however, and it is believed that the enkephalins are rapidly destroyed by blood enzymes and/or are poorly transported across the blood-brain barrier.

The amino acid sequence of methionine-enkephalin is identical to that of the N-terminal portion of the C-fragment ($\beta$-endorphin or $\beta$-LPH[61-91]) of the peptide $\beta$-lipotropin, which is found in large concentrations in the pituitary and in much lower concentrations in the brain. Other naturally-occuring fragments of $\beta$-lipotropin are known, for example: $\alpha$-endorphin ($\beta$-LPH[61-76]) and $\gamma$-endorphin ($\beta$-LPH[61-77]). Both $\beta$-lipotropin and the endorphins show morphine-like properties in various test systems, and it has been suggested that methionine-enkephalin is a breakdown product of the large opiate-like peptides. Enkephalin, its relationship to $\beta$-lipotropin and the endorphins, and the pharmacological properties thereof, are reviewed in an article by Iversen et al., Nature, 262, 738 (1976). Recent developments are also described in detail in the "Proceedings of the International Narcotics Research Club Meeting, Aberdeen, U.K., July 19-22, 1976," published in OPIATES AND ENDOGENOUS OPIOID PEPTIDES, North Holland Publishing Company, Amsterdam, 1976.

Various structural variations of methionine-enkephalin and leucine-enkephalin are described in the literature. For example, the pentapeptide H-Tyr-Gly-Gly-Phe-Thr-OH, wherein the fifth amino acid residue (methionine or leucine) is replaced by threonine, is described by Chang et al., Life Sciences, 18, 1473 (1976).

DESCRIPTION OF THE INVENTION

The present invention relates to a structural modification of $\beta$-LPH[61-76] wherein L-leucyl is introduced in position 65. In accordance with the invention there is provided a polypeptide of the formula:

H-Tyr-Gly-Gly-Phe-Leu-Thr-Ser-Glu-Lys-Ser-Gln-Thr-Pro-Leu-Val-Thr-OH     I or a non-toxic salt thereof. All chiral amino acid residues identified in Formula I, and in the other formulae depicted herein, are in the natural or L-configuration.

The polypeptide of Formula I, or a non-toxic salt thereof, exerts an analgesic effect as demonstrated in rats using the rat-tail flick method of D-Amour and Smith [D'Amour and Smith, J. Pharmacol. Exp. Ther., 72, 74 (1941)] when they are injected directly into the lateral brain ventricle. In this test method, which is a standard test for analgesia, a light beam is focused on the tip of the rat's tail, and the pain threshold of the animal is measured by the latency of the rat to remove his tail from the noxious heat source. When tested by the rat-tail flick method by intracerebroventricular injection, according to the procedure of Belluzzi et al., Nature, 260, 625 (1976), the polypeptides of this invention produced the effects set forth in Table I.

TABLE I

| Drug* | Dose | No. of Rats | Mean Latency ± SEM Baseline | Mean Latency ± SEM Drug | Mean % Change ± SEM |
|---|---|---|---|---|---|
| Ringer's Solution (pH 4.0) | — | 13 | 4.−2 ± 0.20 | 4.27 ± 0.28 | 6.6 ± 6.9 |
| $\beta$-LPH 61-76 (Leu$^{65}$) | 10 μg | 2 | 3.24 ± 0.18 | 4.33 ± 0.05 | 34.32 ± 8.75 |
|  | 100 μg | 3 | 3.39 ± 0.05 | 6.26 ± 0.96 | 86.02 ± 30.79 |
|  | 200 μg | 1 | 4.03 | 4.16 | 3.04 |
| $\beta$-LPH 61-76 | 20 μg | 1 | 3.57 | 2.50 | −29.92 |
| ($\alpha$-endorphin) | 100 μg | 3 | 3.25 ± 0.07 | 6.83 ± 0.89 | 109.15 ± 24.63 |
| Leucine-Enkephalin | 100 μg | 11 | 3.97 ± 0.17 | 5.11 ± 0.34 | 31.7 ± 11.5 |
| Methionine-Enkaphalin | 100 μg | 24 | 3.83 ± 0.14 | 5.19 ± 0.31 | 37.2 ± 8.8 |
| Morphine | 10 μg | 7 | 3.96 ± 0.42 | 6.59 ± 0.73 | 65.4 ± 9.1 |

*All drugs were dissolved in 10 ml. of Ringer's solution and injected into the lateral ventricle through permanently-indwelling cannulae.

The results in Table I show that injection of the polypeptide of this invention into the lateral brain ventricle produced an increase in pain threshold as indicated by the significant difference between the mean % change in latency for the drug (drug minus baseline) and the mean % change in latency for the vehicle (Ringer's solution minus baseline). It has been found that the polypeptide of this invention exhibits weak binding to opiate receptors in vitro and is capable of displacing 3H-naloxone from binding sites in rat brain homogenates, activity consistent with an opiate-like analgesic effect. At a dose as low as 10 μg, the compound of this invention is active, producing an analgesic effect of very long duration (>2 hours).

Also contemplated by this invention are the salts of the polypeptide of Formula I with non-toxic, pharmaceutically acceptable acids. Suitable acids, both organic and inorganic, will be readily apparent to one skilled in the art, for example: hydrochloric, hydrobromic, sulfonic, phosphoric, maleic, acetic, citric, benzoic, succinic, malic, ascorbic, and the like. The salts are prepared and isolated by conventional methods.

The symbols used for representing the amino acid residues in Formula I and in the other formulae employed herein are defined according to the IUPAC-IUB Commission on Biochemical Nomenclature Recommendations (1971), Archives of Biochemistry and Biophysics, 150, 1–8 (1972).

The polypeptide of Formula I is prepared by solid-phase techniques well known in the art of peptide chemistry. The method of synthesis is illustrated in the following examples.

EXAMPLE 1

$N^\alpha$-tert-butyloxycarbonyl-O-2,6-dichlorobenzyl-L-tyrosyl-glycyl-glycyl-L-phenylalanyl-L-laucyl-O-benzyl-L-threonyl-O-benzyl-L-seryl-$\gamma$-benzyl-L-glutamyl-$N^\epsilon$-2-chlorobenzyloxycarbonyl-L-lysyl-O-benzyl-L-seryl-L-glutaminyl-O-benzyl-L-threonyl-L-prolyl-L-leucyl-L-valyl-O-benzyl-L-threonyl-hydroxymethyl-polystyrene ester.

Chloromethylated polystyrene resin (Lab Systems, Inc.) 1% cross-linked with divinylbenzene was esterified with Boc-Thr(Bzl)-OH according to Gisin, *Helv. Chim. Acta* 56, 1976 (1973). The polystyrene resin ester was treated according to schedule A for the incorporation of Boc-Val-OH, Boc-Leu-OH, Boc-Pro-OH, Boc-Thr(Bzl)-OH, Boc-Gln-OH, Boc-Ser(Bzl)-OH, Boc-Lys(ClZ)-OH, Boc-Glu(Bzl)-OH, Boc-Ser(Bzl-OH, Boc-Thr(Bzl)-OH, Boc-Leu-OH, Boc-Phę-OH, Boc-Gly-OH and Boc-Tyr(Cl$_2$Bzl)-Gly-OH, to afford the title peptido resin.

Schedule A

1. Wash with CH$_2$Cl$_2$ × 3.
2. Treat with TFA-CH$_2$Cl$_2$-EDT (1:1:5%, v/v) for 5 min.
3. Treat as in 2 for 25 min.
4. Wash with CH$_2$Cl$_2$ × 3.
5. Wash with DMF.
6. Treat with 12% TEA in DMF twice for 3 min.
7. Wash with DMF.
8. Wash with CH$_2$Cl$_2$ × 3.
9. Treat with 4 equivalents of the corresponding amino acid derivative in CH$_2$Cl$_2$-DMF and stir for 5 min.
10. Add in two portions 5 equivalents of DIC dissolved in CH$_2$Cl$_2$ and over a period of 30 min. Reaction time 6 hours.
11. Wash with DMF × 3.
12. Wash with CH$_2$Cl$_2$ × 3.
13. Test ninhydrin reaction according to Kaiser et al., *Annal. Biochem,* 34, 595 (1970). In case of incomplete reaction repeat lines 9 to 13 as above.

EXAMPLE 2

L-Tyrosyl-glycyl-glycyl-L-phenylalanyl-L-leucyl-L-threonyl-L-seryl-L-glutamyl-L-lysyl-L-seryl-L-glutaminyl-L-threonyl-L-prolyl-L-leucyl-L-valyl-L-threonine.

The peptidoresin of the previous example (6 g) was mixed with anisole (20 ml.) and treated with liquid HF for 50 minutes in an ice-bath after which time the excess HF was removed under vacuo as fast as possible (ca. 60 minutes). The residue was taken in 10% aq. AcOH, filtered and the filtrate was washed with ether. The aqueous layer was passed through a column of Bio Rad AG$_3$ (acetate form) and lyophilized to afford crude material (425 mg).

The crude material was purified by partition chromatography through a Sephadex G 25 (2.5 × 55 cm) column equilibrated first with the lower phase of a biphasic system, n-butanol-water-gl. AcOH, 4:5:1 then with the upper phase. During elution with the upper phase, the desired title peptide emerged in tubes 30 to 37 (300 drops each tube).

$R_f$ (BWA, 2:1:1) 0.67 $R_f$ (BWA, 4:1:1) 0.34, avicel precoated plates.

Amino acid analysis: Thr(3), 2.84, Ser (2) 2.06, Glu (2) 2.08, Pro (1) 1, Gly (2) 2, Val (1) 1, Leu (2) 2.03, Tyr (1) 0.95, Phe (1) 1, Lys (1) 1.04, NH$_3$ (1) 1.5.

What is claimed is:

1. A polypeptide of the formula:

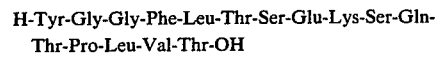

H-Tyr-Gly-Gly-Phe-Leu-Thr-Ser-Glu-Lys-Ser-Gln-Thr-Pro-Leu-Val-Thr-OH or a non-toxic salt thereof, all optically active amino acids being of the L-configuration.

2. The compound of claim 1 which is: L-Tyrosyl-glycyl-glycyl-L-phenylalanyl-L-leucyl-L-threonyl-L-seryl-L-glutamyl-L-lysyl-L-seryl-L-glutaminyl-L-threonyl-L-prolyl-L-leucyl-L-valyl-L-threonine.

* * * * *